US006555133B2

(12) United States Patent
Makooi-Morehead et al.

(10) Patent No.: US 6,555,133 B2
(45) Date of Patent: Apr. 29, 2003

(54) FORMULATION OF FAST-DISSOLVING EFAVIRENZ CAPSULES OR TABLETS USING SUPER-DISINTEGRANTS

(75) Inventors: William T. Makooi-Morehead, Wallingford, PA (US); John D. Buehler, Ambler, PA (US); Brian R. Landmann, Hoboken, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/824,071

(22) Filed: Apr. 2, 2001

(65) Prior Publication Data

US 2001/0012518 A1 Aug. 9, 2001

Related U.S. Application Data

(63) Continuation of application No. 09/286,902, filed on Apr. 6, 1999, now Pat. No. 6,238,695.
(60) Provisional application No. 60/080,925, filed on Apr. 7, 1998.

(51) Int. Cl.[7] .............................. A61K 9/20; A61K 9/48
(52) U.S. Cl. ..................... 424/451; 424/452; 424/464; 424/465; 514/772.3; 514/778; 514/781; 514/885
(58) Field of Search .................. 424/451, 464, 424/465, 452, 456, 466, 468, 470, 472

(56) References Cited

U.S. PATENT DOCUMENTS

| 5,519,021 A | 5/1996 | Young et al. |
| 6,238,695 B1 * | 5/2001 | Makooi-Morehead et al. ........................ 424/451 |

FOREIGN PATENT DOCUMENTS

| EP | 0301006 | 2/1987 |
| EP | 0394553 | 10/1990 |
| HU | 207950 | 8/1991 |
| WO | WO 9520389 | 8/1994 |
| WO | WO 9622955 | 8/1996 |
| WO | WO 9641634 | 12/1996 |
| WO | WO 8705804 | 10/1997 |
| WO | WO 9961026 | 12/1999 |

OTHER PUBLICATIONS

John E. Botzolakis and Larry L. Augsburger, 1988, Disintegrating Agents in Hard Gelatin Capsules, Drug Development and Industrial Pharmacy, 14(1), 29–41.
Bolhuis et al., 1997, European Journal of Pharmaceutical Science, 5(2), 63–69.
Te Wiernik, et al., 1992, ACTA Pharm Nord, 4(4), 239–44.
Remington's Pharmaceutical Sciences 19th. Edition, p. 1619 (1995).

* cited by examiner

Primary Examiner—James M. Spear
(74) Attorney, Agent, or Firm—Paul D. Golian

(57) ABSTRACT

The present invention provides improved oral dosage form formulations of efavirenz that are useful in the inhibition of human immunodeficiency virus (HIV), the prevention or treatment of infection by HIV, and in the treatment of the resulting acquired immune deficiency syndrome (AIDS). In particular, the present invention relates to compressed tablets or capsules comprising efavirenz that contain one or more disintegrants that enhance the dissolution rate of the efavirenz in the gastrointestinal tract thereby improving the rate and extent of absorption of efavirenz in the body. The present invention also relates to the process of making such tablets or capsules.

15 Claims, No Drawings

FORMULATION OF FAST-DISSOLVING EFAVIRENZ CAPSULES OR TABLETS USING SUPER-DISINTEGRANTS

This application is a continuation of U.S. patent application Ser. No. 09/286,902, filed Apr. 6, 1999, which is now U.S. Pat. No. 6,238,695, and claims benefit of U.S. provisional application No. 60/080,925, filed Apr. 7, 1998.

FIELD OF THE INVENTION

The present invention provides improved oral dosage form formulations of efavirenz that are useful in the inhibition of human immunodeficiency virus (HIV), the prevention or treatment of infection by HIV, and in the treatment of the resulting acquired immune deficiency syndrome (AIDS). In particular, the present invention relates to compressed tablets or capsules comprising efavirenz that contain one or more disintegrants that enhance the dissolution rate of the efavirenz in the gastrointestinal tract thereby improving the rate and extent of absorption of efavirenz in the body. The present invention also relates to the process of making such tablets or capsules.

BACKGROUND OF THE INVENTION

In the dose titration of a patient, the objective is to attain and maintain a blood level of drug substance that exceeds the minimum effective level required for response but does not exceed the minimum toxic level. Absorption of a drug from an oral dosage form such as a tablet or a capsule can be affected by properties of the formulation and its method of manufacture. This is particularly true when the drug has low solubility in water, has a hydrophobic nature, and/or is administered in high therapeutic doses. In such cases, dissolution of the drug from the dosage form in the gastrointestinal tract can be the limiting factor that determines the rate and extent of absorption of drug into the body. Changes in the composition and/or method of manufacture of the dosage form can affect the dissolution rate.

An active area of research is in the discovery of new methods of drug formulation. Drug release from a solid dosage form can be enhanced by addition of materials referred to as disintegrants. Disintegrants are substances or a mixture of substances added to the drug formulation that facilitate the breakup or disintegration of the tablet or capsule contents into smaller particles that dissolve more rapidly than in the absence of the disintegrant (Handbook of Pharmaceutical Excipients, Ainley Wade and Paul J. Weller eds., 2d ed. 1994; The Theory and Practice of Industrial Pharmacy, Leon Lachman, Herbert A. Lieberman, and Joseph L. Kanig eds., 3rd ed. 1986; Disintegrating Agents in Hard Gelatin Capsules, John E. Botzolakis and Larry L. Augsburger, Drug Development and Industrial Pharmacy 14(1), 29–41 1988). Materials that serve as disintegrants include starches, clays, celluloses, algins, gums and cross-linked polymers. A group of disintegrants referred to as "super-disintegrants" are generally used at a low level in the solid dosage form, typically 1 to 10% by weight relative to the total weight of the dosage unit. Examples of super-disintegrants are croscarmellose, crospovidone and sodium starch glycolate, which represent examples of a cross-linked cellulose, a cross-linked polymer and a cross-linked starch, respectively. EP 0,301,006 describes the use of super-disintegrants to enhance the dissolution properties of tablet and capsule formulations containing methylprednisolone, a glucocorticoid steroid.

It is desirable to develop formulations where the tablet or capsule disintegrates rapidly and the pharmaceutical agent dissolves readily. This is especially important where the pharmaceutical agent is highly insoluble and/or must be administered in high-strength dosage forms.

This invention relates to new solid oral dosage form formulations containing the HIV drug efavirenz that enhance the dissolution rate of efavirenz in the gastrointestinal tract in order to improve the rate and extent of absorption into the body, thereby improving its therapeutic effect.

SUMMARY OF THE INVENTION

The present invention provides improved solid dosage forms containing the non-nucleoside HIV reverse transcriptase inhibitor (NNRTI) drug efavirenz that disintegrate and dissolve rapidly thereby enhancing the therapeutic characteristics of the formulation. The present invention also provides processes for the manufacture of capsule and tablet formulations of efavirenz that allow a significantly higher strength of efavirenz to be formulated in a single capsule or tablet.

An embodiment of the present invention includes formulations and processes for manufacturing tablets or capsules containing efavirenz using a high-shear, wet granulation step where a very high level of a super-disintegrant such as sodium starch glycolate is included in the wet granulation step.

Another embodiment of the present invention uses the super-disintegrant sodium starch glycolate in both a wet granulation and a dry blending step in the manufacturing process of tablets and capsules containing efavirenz. In a preferred embodiment of the manufacturing process the quantity of the sodium starch glycolate used in the wet granulation step is in the range from about 20% to about 75% by weight relative to the total dry weight of materials being granulated in the wet granulation step. More preferably the super-disintegrant component in the wet granulation step is in the range from about 20% to about 55% by weight relative to the total dry weight of the materials being granulated in the wet granulation step.

In another embodiment of the present invention the range for the efavirenz in the wet granulation step can vary from about 25% to about 80% by weight relative to the total dry weight of the materials being granulated in the wet granulation step. More preferably the drug substance component will range from about 45% to about 80% by weight relative to total dry weight of the ingredients in the wet granulation step.

In the present invention a surfactant such as sodium lauryl sulfate is preferably used in the wet granulation step of the process for the manufacture of the capsules or tablets of the present invention. The sodium lauryl sulfate is preferably dissolved in the wet granulating fluid. Most preferably the sodium lauryl sulfate will range from about 0.1% to about 5% by weight relative to the total dry weight of the materials being granulated in the wet granulation step.

DETAILED DESCRIPTION OF THE INVENTION

The present invention provides improved oral dosage form formulations of efavirenz that are useful in the inhibition of human immunodeficiency virus (HIV), the prevention or treatment of infection by HIV, and in the treatment of the resulting acquired immune deficiency syndrome (AIDS). In particular, the present invention relates to compressed tablets or capsules comprising efavirenz that contain one or more disintegrants that enhance the dissolution rate of the efavirenz in the gastrointestinal tract thereby improving the rate and extent of absorption of efavirenz in the body. The present invention also relates to the process of making such tablets or capsules.

The active ingredient of the formulation of the present invention is the NNRTI efavirenz, which is present in a therapeutically effective amount. Methods for the manufacture of efavirenz are disclosed in U.S. Pat. No. 5,519,021. The disclosure of U.S. Pat. No. 5,519,021 in its entirety is hereby incorporated by reference. Efavirenz is (s)6-chloro-4-(cyclopropylethynyl)-1,4-dihydro-4-(trifluoromethyl)-2H-3,1-benzoxazin-2-one.

In addition to the active ingredient, solid dosage forms contain a number of additional ingredients referred to as excipients. These excipients include among others diluents, binders, lubricants, glidants and disintegrants. Diluents are used to impart bulk to the formulation to make a tablet a practical size for compression. Examples of diluents are lactose and cellulose. Binders are agents used to impart cohesive qualities to the powered material ensuring the tablet will remain intact after compression, as well as improving the free-flowing qualities of the powder. Examples of typical binders are lactose, starch and various sugars. Lubricants have several functions including preventing the adhesion of the tablets to the compression equipment and improving the flow of the granulation prior to compression or encapsulation. Lubricants are in most cases hydrophobic materials. Excessive use of lubricants can result in a formulation with reduced disintegration and/or delayed dissolution of the drug substance. Glidants are substances that improve the flow characteristics of the granulation material. Examples of glidants include talc and colloidal silicon dioxide. Disintegrants are substances or a mixture of substances added to a formulation to facilitate the breakup or disintegration of the solid dosage form after administration. Materials that serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmellose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it. Granulation refers to a mixing technique by which the overall particle size of a formulation is increased through the permanent aggregation of smaller particles. Wet granulation refers to granulation that is accomplished by wetting the smaller particles so they tack to one another. The newly-formed larger particles remain intact after drying. In dry granulation, larger particles are formed as a result of the compaction of the dry ingredients, followed by milling of this compacted material into suitably sized particles.

An embodiment of the present invention is a formulation and a process for manufacturing tablets or capsules using a high-shear, wet granulation step in which a very high level of a super-disintegrant such as sodium starch glycolate is included, followed by a dry blending step that incorporates additional quantities of super-disintegrant. In the present invention the amount of the super-disintegrant in the wet granulation step of the manufacturing process is preferably in the range of about 20% to about 75% by weight relative to the total dry weight of the materials used in the wet granulation step. More preferably the super-disintegrant component will range from about 20% to about 55% by weight relative to the total dry weight of all of the ingredients in the wet granulation step of the manufacturing process. In general, the range for the HIV reverse transcriptase inhibitor in the wet granulation step can vary from about 25% to about 80% by weight relative to the total dry weight of all of the ingredients in the wet granulation step of the manufacturing process. More preferably the drug substance component will range from about 45% to about 80% by weight relative to the total dry weight of all of the ingredients in the wet granulation step of the manufacturing process. Also included in the wet granulation step is a surfactant such as sodium lauryl sulfate, or another material that improves the wettability of the drug. Preferably the surfactant component will range from about 0.1% to about 5% by weight relative to the total weight of ingredients in the formulation. After the wet granulation step, the material is dried, milled, and dry blended with other ingredients such as diluents, glidants, disintegrants, and lubricants. The result of the dry blending step is then filled into gelatin capsule shells or compressed into tablets. Gelatin capsules may contain the active ingredient and powdered carriers such as lactose, starch, cellulose derivatives, magnesium stearate, stearic acid, and the like. Similar diluents can be used to make compressed tablets. Both capsules and tablets can be manufactured as sustained release products to provide for continuous release of medication over a period of hours. Compressed tablets can be sugar coated or film coated to mask any unpleasant taste and to protect the tablet from the atmosphere, or enteric coated for selective disintegration in the gastrointestinal tract. Technology for the formation of solid dosage forms such as capsules and compressed tablets, that utilize conventional pharmaceutical manufacturing equipment for their purpose, is described in detail in Remington's Pharmaceutical Sciences (Alfonso R. Gennaro ed., ch. 89, 18th ed. 1990).

In one aspect of the present invention, it was discovered that the sodium starch glycolate acts as a highly swellable carrier material onto which the efavirenz adheres during the wet granulation step of the process for the manufacture of tablets or capsules containing efavirenz. Granulation refers to a processing technique by which the overall particle size of a formulation is increased through the permanent aggregation of smaller particles. Wet granulation refers to granulation that is accomplished by wetting the smaller particles so they tack to one another. The newly-formed larger particles remain intact after drying. In the dry blending step of the process for the manufacture of tablets or capsules containing efavirenz, extragranular materials are added to the granulation to impart other improved characteristics such as flow and lubricity. The granulation is evenly blended throughout the mixture.

The adherence of the drug efavirenz substance particles to the hydrated disintegrant sodium starch glycolate is accomplished by intimate mixing in the wet granulation step. In an embodiment of the present invention the quantity of sodium starch glycolate used in the wet granulation step is significantly higher than is typically used. In the present invention the wet granulation preferably contains about 20% to about 75% by weight sodium starch glycolate relative to the total dry weight of the ingredients of the wet granulation step, as opposed to the 1–10% that is used in a typical wet granulation step (Handbook of Pharmaceutical Excipients, Ainley Wade and Paul J. Weller eds., 2d ed. 1994; The Theory and Practice of Industrial Pharmacy, Leon Lachman, Herbert A. Lieberman, and Joseph L. Kanig eds., 3rd ed. 1986; Disintegrating Agents in Hard Gelatin Capsules, John E. Botzolakis and Larry L. Augsburger, Drug Development and Industrial Pharmacy 14(1), 29–41 1988). During the wet granulation, efavirenz drug substance particles are attached to the surface of the sodium starch glycolate particles. When these granules are exposed to the fluid in the gastrointestinal tract following the disintegration of the solid dosage form, the sodium starch glycolate rapidly swells and presents the attached efavirenz drug substance particles to the fluid allowing for rapid dissolution of the efavirenz.

The present invention provides capsule or compressed tablet pharmaceutical dosage forms comprising a therapeutically effective amount of efavirenz and comprising one or more disintegrants in an amount greater than about 10% by weight relative to the total weight of the contents of the capsule or the total weight of the tablet.

The disintegrant used in the present invention is preferably selected from the group comprising modified starches, croscarmellose sodium, carboxymethylcellulose calcium and crospovidone.

The preferred disintegrant in the present invention is a modified starch.

The more preferred disintegrant in the present invention is the modified starch sodium starch glycolate.

In the present invention the capsule formulation contains efavirenz present in an amount from about 5 to about 1000 mg per capsule.

It is preferred in the present invention that the capsule formulation contain from about 5 to about 500 mg of efavirenz per capsule.

It is preferred in the present invention that the capsule formulation contain from about 500 to about 1000 mg of efavirenz per capsule.

It is preferred in the present invention that the capsule formulation contain from about 25 to about 350 mg of efavirenz per capsule.

It is preferred in the present invention that the capsule formulation contain from about 50 to about 200 mg of efavirenz per capsule.

The compressed tablet of the present invention contains efavirenz in an amount from about 5 to about 800 mg per tablet.

The present invention provides for a pharmaceutical dosage form comprising:

(a) a therapeutically effective amount of efavirenz;
(b) a surfactant;
(c) a disintegrant;
(d) a binder;
(e) a diluent;
(f) a lubricant;
(g) a glidant; and
(h) optionally additional pharmaceutically acceptable excipients;

wherein the disintegrant is selected from modified starches, croscarmellose sodium, carboxymethylcellulose calcium and crospovidone and is present in an amount greater than about 10% by weight of the total dry weight of the capsule contents or the compressed tablet.

Another embodiment of the present invention provides a method for manufacturing a solid dosage form comprising the steps of:

(a) wet granulating the efavirenz and the intragranular sodium starch glycolate in a high-shear granulator using an aqueous solution of sodium lauryl sulfate;
(b) drying result of step (a);
(c) milling result of step (b);
(d) dry blending result of step (c) with the extragranular sodium starch glycolate and additional pharmaceutically acceptable excipients; and
(e) encapsulating or compressing into tablets the result of step (d).

As used herein, the following terms and expressions have the indicated meanings.

"Sodium starch glycolate" refers to sodium carboxymethyl starch.

"Efavirenz" refers to the pharmacologically active ingredient (S)6-chloro-4-(cyclopropylethynyl)-1,4-dihydro-4-(trifluoromethyl)-2H-3,1-benzoxazin-2-one. The process for the synthesis of this compound is described in U.S. Pat. No. 5,519,021, which is hereby incorporated by reference.

"Therapeutically effective amount" is intended to mean an amount of a compound sufficient to produce the desired pharmacological effect.

"Modified starch" as used herein means any of several water-soluble polymers derived from a starch (corn, potato, tapioca) by acetylation, chlorination, acid hydrolysis, or enzymatic action.

EXAMPLES

In the following embodiments of the invention, the below-listed quantities of drug substance and additional components are combined using standard pharmaceutical manufacturing techniques. The resulting formulations are used to fill gelatin capsule shells or compressed into tablets utilizing standard pharmaceutical manufacturing techniques.

Example 1

Wet Granulation 100 mg Capsule Formulation

Method of manufacture: The efavirenz and intragranular sodium starch glycolate are mixed and then wet granulated after adding an aqueous solution of sodium lauryl sulfate. This wet mass may then be dried in a fluid bed, tray or other suitable dryer. The dried granulation may then be milled to achieve a suitable particle size distribution and then is blended with the other ingredients. This blend is then filled into two piece hard gelatin capsule shells.

| Ingredient | Amount per capsule | % |
|---|---|---|
| efavirenz | 100 mg | 39.06 |
| sodium lauryl sulfate | 5 mg | 1.95 |
| lactose, hydrous | 57 mg | 22.26 |
| magnesium stearate | 4 mg | 1.56 |
| sodium starch glycolate (intragranular) | 80 mg | 31.25 |
| sodium starch glycolate (extragranular) | 10 mg | 3.91 |
| Total Capsule Weight | 256 mg | |

Example 2

Wet Granulation 100 mg Capsule Formulation

Method of manufacture: The efavirenz and intragranular sodium starch glycolate are granulated using an aqueous solution of sodium lauryl sulfate. This wet mass may then be dried in a fluid bed, tray or other suitable dryer. The dried granulation may then be milled to achieve a suitable particle size distribution and then is blended with the other ingredients. This blend is then filled into two piece hard gelatin capsule shells.

| Ingredient | Amount per capsule | % |
|---|---|---|
| efavirenz | 100 mg | 21.93 |
| sodium lauryl sulfate | 5 mg | 1.10 |
| sodium starch glycolate (intragranular) | 50 mg | 10.96 |
| sodium starch glycolate (extragranular) | 10 mg | 2.19 |
| lactose, hydrous | 277 mg | 60.75 |
| talc | 8 mg | 1.75 |
| colloidal silicon dioxide | 4 mg | 0.88 |
| stearic acid | 2 mg | 0.44 |
| Total Capsule Weight | 456 mg | |

Example 3

Wet Granulation 300 mg Tablet Formulation

Method of manufacture: The efavirenz, sodium starch glycolate and microcrystalline cellulose are granulated using an aqueous solution of sodium lauryl sulfate. This wet mass may then be dried in a fluid bed, tray or other suitable dryer. The dried granulation may then be milled to achieve the desired particle size distribution. This blend is compressed into tablets. These tablets may be coated if desired.

| Ingredient | Amount per tablet | % |
|---|---|---|
| efavirenz | 300 mg | 50.00 |
| sodium lauryl sulfate | 12 mg | 2.00 |
| microcrystalline cellulose | 120 mg | 20.00 |
| sodium starch glycolate | 120 mg | 20.00 |
| lactose, hydrous | 42 mg | 7.00 |
| magnesium stearate | 6 mg | 1.00 |
| Total Tablet Weight | 600 mg | |

Assays were performed on capsule and tablet samples taken during the manufacturing processes described above. Analyses of the capsules and tablets utilized USP specified procedures. The dissolution test used USP methodology Apparatus 2 (paddles at 50 RPM, 900 mL of 1% sodium lauryl sulfate-distilled water solution at 37° C.)

TABLE 1

Dissolution Assay of Capsule Formulation
Capsule Formulation of Example 1:

| Time (minutes) | % Dissolved |
|---|---|
| 10 | 82.9 |
| 15 | 94.6 |
| 30 | 98.5 |
| 45 | 99.3 |
| 60 | 99.6 |

TABLE 2

Dissolution Assay of Tablet Formulation
Tablet Formulation of Example 3:

| Time (minutes) | % Dissolved |
|---|---|
| 10 | 78.0 |
| 15 | 91.5 |
| 30 | 100.0 |
| 45 | 102.1 |
| 60 | 102.9 |

Assays were performed to determine dosage-form uniformity on capsule and tablet samples taken during the manufacturing processes described above. Capsules and tablets were tested for content uniformity following USP specified guidelines. Results are shown in Table 3. "RSD" as used herein refers to relative standard deviation and is calculated according to USP guidelines.

TABLE 3

Content Uniformity Assay

| Capsules from Example 1: content uniformity | 100.2 ± 1.7% (mean ± RSD) |
|---|---|
| Tablets from Example 3: content uniformity | 104.3 ± 0.7% (mean ± RSD) |

What is claimed is:

1. A method for treating infection by HIV comprising administering to a patient, in need of such treatment, a capsule or a compressed tablet pharmaceutical dosage form comprising a therapeutically effective amount of efavirenz and greater than about 10% by weight of a disintegrant relative to the total dry weight of the pharmaceutical dosage form.

2. A method for treating infection by HIV according to claim 1, wherein at least one disintegrant is selected from the group consisting of modified starches, croscarmellose sodium, carboxymethylcellulose calcium and crospovidone.

3. A method for treating infection by HIV according to claim 2, wherein the disintegrant is selected from one or more modified starches.

4. A method for treating infection by HIV according to claim 3, wherein the modified starch is sodium starch glycolate.

5. A method for treating infection by HIV according to claim 3 wherein the capsule or compressed tablet pharmaceutical dosage form is prepared using a wet granulation step containing efavirenz and one or more modified starches, wherein the modified starch is present in the wet granulation step in an amount of from about 10% to about 75% by weight relative to the total dry weight of the components of the wet granulation step.

6. A method for treating infection by HIV according to claim 3 wherein the modified starch is present in the wet granulation step of the manufacturing process in an amount of from about 20% to about 55% by weight relative to total dry weight of the components of the wet granulation step.

7. A method for treating infection by HIV according to claim 1 wherein the efavirenz is present in the pharmaceutical dosage form in an amount of from about 5 to about 1000 mg.

8. A method for treating infection by HIV according to claim 1 wherein the efavirenz is present in the pharmaceutical dosage form in an amount of from about 5 to about 500 mg.

9. A method for treating infection by HIV according to claim 1 wherein the efavirenz is present in the pharmaceutical dosage form in an amount of from 500 to about 1000 mg.

10. A method for treating infection by HIV according to claim 1 wherein the efavirenz is present in the pharmaceutical dosage form in an amount of from about 25 to about 350 mg.

11. A method for treating infection by HIV according to claim 1 wherein the efavirenz is present in the pharmaceutical dosage form in an amount of from about 50 to about 200 mg.

12. A method for treating infection by HIV according to claim 5 or 6, wherein the wet granulation step is carried out in the presence of sodium lauryl sulfate.

13. A method for treating infection by HIV according to claim 12, wherein the sodium lauryl sulfate is present in an amount of about 0.1% to about 5% by weight relative to total dry weight of the components of the wet granulation step.

14. A method for treating infection by HIV according to claim 1, wherein the efavirenz is present in the pharmaceutical dosage form in an amount of from about 5 to about 800 mg.

15. A method for treating infection by HIV comprising administering to a patient, in need of such treatment, a pharmaceutical dosage form comprising:

(a) a therapeutically effective amount of efavirenz;

(b) a surfactant;

(c) a disintegrant;

(d) a binder;

(e) a diluent;

(f) a glidant; and (g) optionally additional pharmaceutically acceptable excipients; wherein at least one disintegrant is selected from the group consisting of modified starches, croscarmellose sodium, carboxymethylcellulose calcium and crospovidone and such disintegrant is present in an amount greater than about 10% by weight of the total dry weight of the capsule contents or the compressed tablet.

* * * * *